United States Patent

Rydgren et al.

[11] Patent Number: 5,871,009
[45] Date of Patent: Feb. 16, 1999

[54] METHOD AND APPARATUS FOR MIXING A GAS CONTAINING NITRIC OXIDE WITH A GAS CONTAINING OXYGEN

[75] Inventors: Göran Rydgren, Bunkeflostrand; Lars Lindberg, Barsebäck, both of Sweden

[73] Assignee: Siemens Elema AB, Solna, Sweden

[21] Appl. No.: 906,298

[22] Filed: Aug. 5, 1997

[30] Foreign Application Priority Data

Aug. 12, 1996 [SE] Sweden .................................. 9602959

[51] Int. Cl.⁶ .................................................. A61M 15/00
[52] U.S. Cl. .............................. 128/203.12; 128/203.14; 128/203.25; 128/203.22; 128/204.22
[58] Field of Search ..................... 128/203.12, 203.14, 128/204.23, 204.21, 203.22, 203.24, 203.25, 204.22

[56] References Cited

U.S. PATENT DOCUMENTS

| 4,936,297 | 6/1990 | Greiff et al. ......................... 128/203.25 |
| 5,427,797 | 6/1995 | Frostell et al. ............................ 424/434 |
| 5,522,381 | 6/1996 | Olsson et al. ........................ 128/203.25 |
| 5,531,218 | 7/1996 | Krebs .................................... 128/203.25 |
| 5,558,083 | 9/1996 | Bathe et al. ........................ 128/203.1 X |
| 5,619,986 | 4/1997 | Werner et al. ....................... 128/204.22 |

FOREIGN PATENT DOCUMENTS

| 0 640 357 | 3/1995 | European Pat. Off. . |
| 0 659 445 | 6/1995 | European Pat. Off. . |
| 502 724 | 10/1994 | Sweden . |
| WO 92/10228 | 6/1992 | WIPO . |
| WO 96/11718 | 4/1996 | WIPO . |

*Primary Examiner*—John G. Weiss
*Assistant Examiner*—V. Srivastava
*Attorney, Agent, or Firm*—Hill & Simpson

[57] ABSTRACT

During the administration of NO to a patient, NO reacts with oxygen in the respiratory gas to form $NO_2$. Since $NO_2$ is a toxic gas, minimizing the formation of this gas is important. A previously unknown property of NO is that an initial amount of $NO_2$ is formed when NO and $O_2$ mix. By adding NO to respiratory gas at a number of spaced-apart mixing points, the total initial amount of $NO_2$ formed can be reduced. In a method and a device for mixing and administering NO, the gas containing NO is supplied to a flow divider for distributing the flow and sending sub-flows to a number of various mixing points.

8 Claims, 1 Drawing Sheet

METHOD AND APPARATUS FOR MIXING A GAS CONTAINING NITRIC OXIDE WITH A GAS CONTAINING OXYGEN

BACKGROUND OF THE INVENTION

1. Field of the Invention

The present invention is directed to a method for mixing a gas containing nitric oxide (NO) with a gas containing oxygen, as well as to an apparatus for conducting the method.

2. Description of the Prior Art

In recent years, the use of gaseous nitric oxide (NO) has attracted widespread interest in different kinds of therapy. A number of positive effects has been found when small amounts of gaseous NO are administered to a patient via the airways. For example, NO has a relaxing effect on smooth muscle, thereby improving oxygenation and reducing blood pressure across the lung in patients with severe pulmonary disease. More extensive descriptions of the effects conveyed by NO are provided in e.g. PCT application WO 92/10228 and U.S. Pat. No. 5,427,797.

NO, usually diluted with $N_2$, is supplied in gas cylinders and is subsequently mixed with a respiratory gas, usually a mixture of air and oxygen ($O_2$), before the final mixture is delivered to the patient. Examples of known administration systems are described in European Application 0 659 445 and Swedish Application 502 724.

The biggest problem with NO is that it is a highly reactive gas and forms, with $O_2$, nitrogen dioxide ($NO_2$)—a highly toxic gas even in small concentrations. Since respiratory gas often contains an elevated concentration of $0_2$, typically 50–80% $O_2$, special measures may be necessary to minimize the amount of $NO_2$ delivered to the patient.

One approach to minimize the opportunity for $NO_2$ to form is to supply the gas containing NO closely as possible to the patient, even inside the patient. This has the disadvantage, however, that the NO and respiratory gases may not have time to mix thoroughly, and a heterogeneous gas mixture could be carried into the lungs.

Another option is to mix the two gases continuously as they flow at a constant rate past an inspiratory line, so that the patient then draws a fresh mixture into her/his lungs at every breath. Implementing this option is difficult, however, when the patient is incapable of spontaneous breathing with an adequate volume. Moreover, large amounts of gas would be consumed, and gas containing NO would have to be evacuated to prevent a rise in the level of $NO_2$ in the room.

Another possibility is to mix the gases in the customary fashion and to install an $NO_2$ absorber or an $NO_2$ filter before the patient. A disadvantage here is the difficulty in determining the supplied concentration of NO. An absorber must be monitored to keep it from becoming saturated, thereby losing its ability to absorb $NO_2$, and a filter must be arranged to keep $NO_2$ from escaping into the room.

Heretofore, the conversion of NO into $NO_2$ was believed to occur in proportion to the squared concentration of NO times the level of $O_2$ times time ($k_2*(NO)^2*O_2*t$). In addition, a small amount Of $NO_2$ may be present in the $O_2$—NO mixture. This amount is proportional to the concentration of NO ($k_0*NO$).

Recently conducted experiments have disclosed an additional factor. NO was found to have a property which causes initial formation of $NO_2$ at the instant of mixture with oxygen, which is proportional only to the square of the NO concentration and the $O_2$ concentration ($k_1*(NO)^2*O_2$).

Thus the final conversion equation, designating the concentration of $NO_2$, is as follows:

$$NO_2 = k_0*NO + k_1*(NO)^2*O_2 + k_2*(NO)^2*O_2*t$$

SUMMARY OF THE INVENTION

An object of the present invention is to utilize this recently discovered phenomenon in the formation of $NO_2$ for achieving a method for minimizing the formation of $NO_2$ when two gases respectively containing NO and $O_2$ are mixed.

Another object of the invention is to provide a device which is designed to minimize the formation of $NO_2$ when two gases respectively containing NO and $O_2$ are mixed.

The above objects are achieved in a method and apparatus according to the invention wherein a first gas, containing nitric oxide, is added to a second gas, containing oxygen, at at least two, and preferably more, mixing points arranged at specified distances from each other.

When gas containing NO is added to gas containing $O_2$ at a number of mixing points, the contribution to the formation of $NO_2$, according to the newly discovered conversion expression, can be reduced. Assume e.g. that the first gas contains 1000 ppm of NO in $N_2$. When it is diluted to form the second gas with a concentration of 100 ppm, $k_1*100^2$ ppm of $NO_2$ are initially formed. If two mixing points are employed, the initial formation (at each point) becomes $k_1*50^2$ ppm of $NO_2$. Total initial formation then becomes $2*(K_1*50^2)$ ppm, i.e., a reduction in initial $NO_2$ by a factor of 2.

DESCRIPTION OF THE PREFERRED EMBODIMENTS

Figure 1:
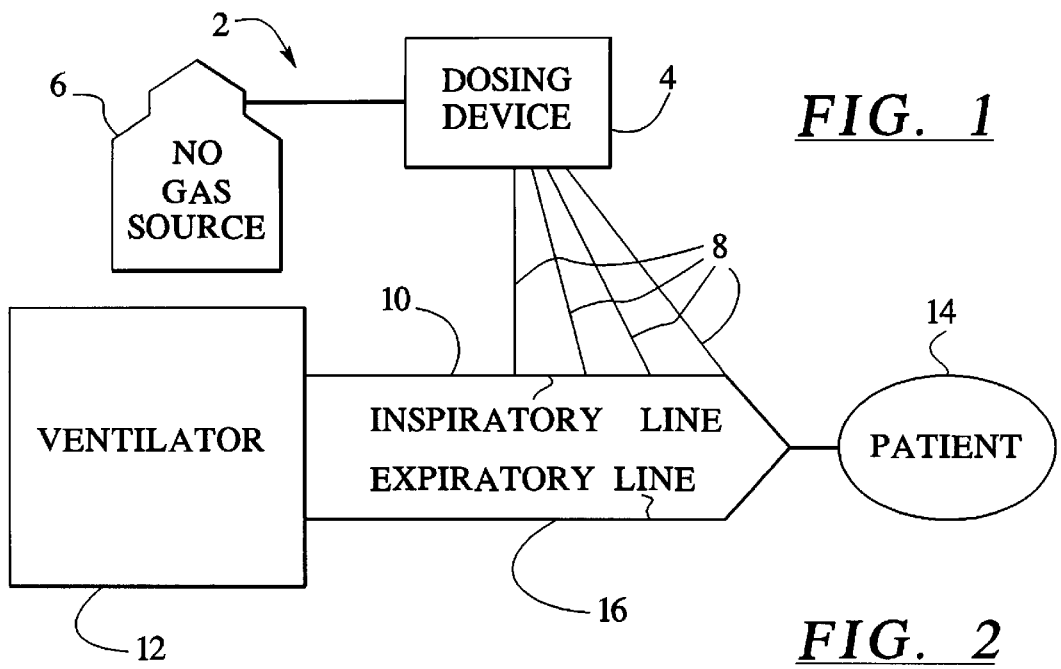
FIG. 1 shows a device constructed and operating according to the present invention connected to a ventilator for dosing NO to a patient.

A system 2 for administering NO to a patient 14 is shown in FIG. 1. The system 2 includes a device 4 for dosing a gas containing NO from a gas source 6 to an inspiratory line 10 via dosing lines 8.

The inspiratory line 10 is connected to a ventilator 12 and carries a respiratory gas from same to the patient 14. The ventilator 12 can be an existing commercially available ventilator such as the Servo Ventilator 300, Siemens-Elema, Solna, Sweden.

Air expired by the patient 14 is carried back to the ventilator 12 in an expiratory line 16.

Figure 2:
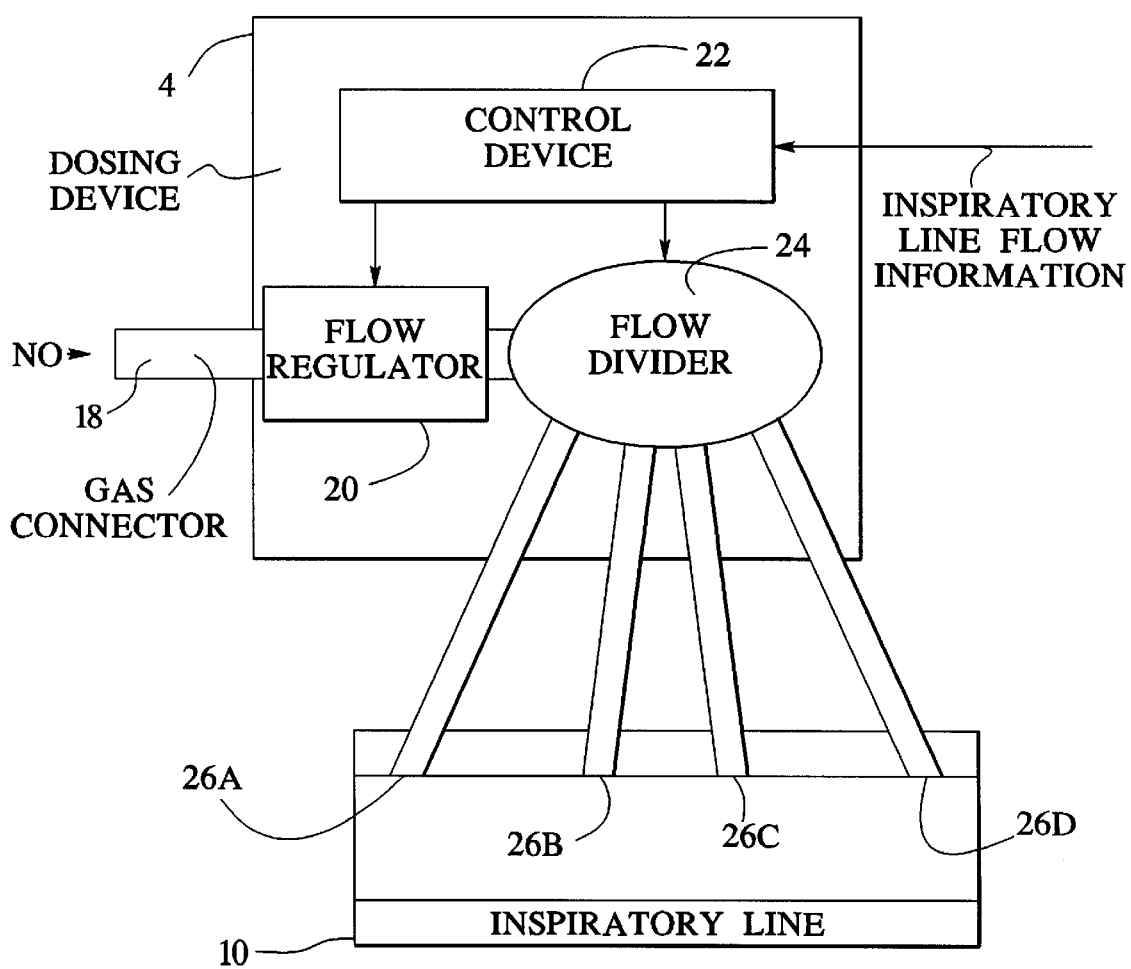
FIG. 2 shows the device of FIG. 1 in greater detail.

As FIG. 2 shows, the device 4 has a gas connector 18, which is coupled to the gas source 6, and a flow regulator 20 for regulating the flow required to achieve a pre-defined concentration of NO in the final mixture supplied to the patient 14. The flow regulator 20 is controlled by a control device 22. As indicated by the arrow in the FIG. 2, the control device 22 receives information about the flow of respiratory gas in the inspiratory line 10 and then controls the flow regulator 20 according to the received flow value and a reference value for the pre-defined concentration. In the known manner, the flow of respiratory gas can be obtained from the ventilator 12 or from a separate flow meter (not shown in the figures).

The dosed flow is carried to a flow divider 24 which distributes this flow via a first mixing point 26A, a second mixing point 26B, a third mixing point 26C and a fourth mixing point 26D, to the inspiratory line 10. The distance between neighboring mixing points within 26A–26D is selected so a homogenous gas mixture is achieved before the next successive mixing point 26B–26D in the direction of respiratory gas flow. The number of mixing points can vary, but two to ten mixing points are appropriate. Too many mixing points 26A–26D could result in needlessly long mixing distances.

Since NO reacts with $O_2$ to form $NO_2$ according to the equation $$NO_2 = k_0 * NO + k_1 * (NO)^2 * O_2 + k_2 * (NO)^2 * O_2 * t$$

in which $k_0$, $k_1$ and $k_2$ are constants, the first term designates the concentration of $NO_2$ in the gas source, the second term designates the initial formation of $NO_2$ in the mixture of gases and the third term designates the time-related formation of $NO_2$ when the gases have been mixed, it can be seen that subdivision into a number of mixing points reduces the second term, i.e. the initial formation of $NO_2$.

Assume that NO is to be supplied to an infant, e.g., a premature neonate with respiratory problems, through an 1.5 m long inspiratory tube. A typical flow would then be one 1/min with an oxygen content of 90% and administration of 100 ppm of NO.

With four mixing points, as in FIG. 2, 10 cm apart and the same dosing flow at each mixing point, a concentration of NO of 25 ppm results after the first mixing point 26A, 50 ppm after the second mixing point 26B, 75 ppm after the third mixing point 26C and 100 ppm after the fourth mixing point 26D. When the first mixing point is 1.5 m from the patient (and the others are at 1.4, 1.3 and 1.2 m), respectively 0.43, 0.42, 0.40 and 0.39 ppm of $NO_2$ are formed at the mixing points. This amounts to a total of 1.63 ppm.

The introduction of 100 ppm of NO at one mixing point at 1.2 m, i.e., the shortest distance, would have resulted in the formation of 4.69 ppm of $NO_2$. In view of the toxicity of $NO_2$ the difference is particularly significant.

Introduction does not have to be into the inspiratory line 10 but can be accomplished in a special mixing chamber or the like. The most important thing is for mixing to occur at a number of mixing points and for homogenous mixing to take place before each new mixing point for the very best results to be achieved.

The distance between the mixing points 26A–26D does not need to be constant, but can vary.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for mixing flowing gases comprises the steps of:
   providing a first gas containing nitric oxide;
   providing a second gas containing oxygen flowing along a flow path; and
   mixing said first gas at a predetermined concentration into said flow path of said second gas with minimized formation of nitrogen dioxide in said flow path, by adding said first gas to said second gas at at least two mixing points disposed at predetermined distances from each other along said flow path.

2. A method as claimed in claim 1 wherein the step of adding said first gas to said second gas comprises adding said first gas at a same flow rate at each of said mixing points.

3. A method as claimed in claim 1 comprising the additional step of selecting said predetermined distances for producing a homogenous mixture of said first gas and said second gas before each successive mixing point in a direction of gas flow along said flow path.

4. A device for mixing flowing gases comprising:
   a gas source containing a first gas containing nitric oxide;
   a flow channel in which a second gas containing oxygen flows;
   at least two mixing points disposed at a predetermined distance from each other along said flow channel; and
   means for supplying said first gas to each of said mixing points for mixing said first and second gases for forming a gas mixture having a predetermined concentration of nitric oxide therein, with minimized formation of nitrogen dioxide in said mixture.

5. A device as claimed in claim 4 wherein said means for supplying said first gas to said mixing points comprises a flow regulator which regulates a total flow of said first gas from said gas source, and a flow divider which distributes said total flow of said first gas to the respective mixing points.

6. A device as claimed in claim 5 wherein said flow divider comprises means for distributing said total flow of said first gas for producing an identical flow of said first gas at each mixing point.

7. A device as claimed in claim 5 wherein said second gas flows at a non-constant flow passed said mixing points, and wherein said flow regulator comprises means for regulating said total flow of said first gas dependent on said flow of said second gas.

8. A device as claimed in claim 4 wherein said flow channel in which said second gas flows comprises an inspiratory tube of a breathing assist system.

* * * * *